(12) United States Patent
Sordillo et al.

(10) Patent No.: US 10,485,768 B2
(45) Date of Patent: Nov. 26, 2019

(54) TREATMENT FOR GLIOBLASTOMA

(71) Applicant: SignPath Pharma Inc., Quakertown, PA (US)

(72) Inventors: Laura A. Sordillo, New York, NY (US); Peter P. Sordillo, New York, NY (US); Lawrence Helson, Quakertown, PA (US)

(73) Assignee: Signpath Pharma, Inc., Sandy, UT (US)

( * ) Notice: Subject to any disclaimer, the term of this patent is extended or adjusted under 35 U.S.C. 154(b) by 0 days.

(21) Appl. No.: 15/265,574

(22) Filed: Sep. 14, 2016

(65) Prior Publication Data
US 2017/0079934 A1 Mar. 23, 2017

Related U.S. Application Data

(60) Provisional application No. 62/220,635, filed on Sep. 18, 2015.

(51) Int. Cl.
| | | |
|---|---|---|
| *A61K 31/121* | (2006.01) | |
| *A61K 45/06* | (2006.01) | |
| *A61K 36/9066* | (2006.01) | |
| *A61K 9/127* | (2006.01) | |
| *A61K 31/4188* | (2006.01) | |
| *A61K 9/00* | (2006.01) | |
| *A61P 35/00* | (2006.01) | |

(52) U.S. Cl.
CPC .......... *A61K 31/121* (2013.01); *A61K 9/0019* (2013.01); *A61K 9/127* (2013.01); *A61K 31/4188* (2013.01); *A61K 36/9066* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 7,015,251 B1 * | 3/2006 | Wanebo ................. | A61K 31/70 424/649 |
| 7,931,922 B2 | 4/2011 | Newmark et al. | |
| 8,518,698 B1 | 8/2013 | Sugaya et al. | |
| 8,945,563 B2 | 2/2015 | Auf Der Maur et al. | |
| 2002/0110586 A1 * | 8/2002 | Madden ................. | A61K 9/127 424/450 |
| 2006/0078631 A1 * | 4/2006 | Newmark ............... | A61K 36/18 424/729 |
| 2010/0197584 A1 * | 8/2010 | Banerjee ............ | A61K 36/9066 514/1.1 |
| 2013/0337488 A1 | 12/2013 | Helson | |
| 2015/0064178 A1 * | 3/2015 | Bais ................. | A61K 39/39558 424/133.1 |

FOREIGN PATENT DOCUMENTS

| | | |
|---|---|---|
| CN | 104758255 A | 7/2015 |
| WO | 200059517 A1 | 10/2000 |
| WO | 2009073050 A2 | 6/2009 |
| WO | 2012167212 A2 | 12/2012 |
| WO | 20130414894 A1 | 3/2013 |

OTHER PUBLICATIONS

Meng, B., et al., "Antioxidant and Antiinflammatory Activities of Curcumin on Diabetes Mellitus and its Complications," Current Pharmaceutical Design, vol. 19, No. 11, Oct. 22, 2012, pp. 2101-2113.
Mishra, S., et al., "The effect of curcumin (turmeric) on Alzheimer's disease: An overview," Ann. Indian Acad. Neurol., vol. 11, Jan.-Mar. 2008, pp. 13-19.
Moussavi, M., et al., "Curcumin mediates ceramide generation via the de novo pathway in colon cancer cells," Carcinogenesis, vol. 27:8, Feb. 25, 2006, pp. 1636-1644.
Nagai, S., et al., "Inhibition of cellular proliferation and induction of apoptosis by curcumin in human malignant astrocytoma cell lines," Journal of Neuro-Oncology, vol. 74, 2005, pp. 105-111.
Nagasawa, D.T., et al., "Temozolomide and other potential agents for the treatment of Glioblastoma Multiforme," Neurosurg. Clin. N. Am., vol. 23:2, 2012, pp. 307-322.
Park, J., et al., "Scale to Predict Survival After Surgery for Recurrent Glioblastoma Multiforme," Journal of Clinical Oncology, vol. 28:24, Aug. 10, 2010, pp. 3838-3843.
Patel, M.A., et al., "The Future of Glioblastoma Therapy: Synergism of Standard of Care and Immunotherapy," Cancers, Sep. 3, 2014, vol. 6, pp. 1953-1985.
Perry, Marie-Claude, et al., "Curcumin inhibits tumor growth and angiogenesis in glioblastoma xenografts," Mol. Nutr. Food Res., Aug. 31, 2009, vol. 54, pp. 1192-1201.
Priyadarsini, K.I., "The Chemistry of Curcumin: From Extraction to Therapeutic Agent," Molecules, vol. 19, Dec. 1, 2014, pp. 20091-20111.
Ramachandran, C., et al., "Potentiation of Etoposide and Temozolomide Cytotoxicity by Curcumin and Turmeric Force in Brain Tumor Cell Lines," vol. 9:1, Article 20, 2012, 16 pp.
Rosso, L., et al., "A New Model for Prediction of Drug Distribution in Tumor and Normal Tissues: Pharmocokinetics at Temozolomide in Glioma Patients," Cancer Res., vol. 69:1, Jan. 1, 2009, pp. 120-127.

(Continued)

*Primary Examiner* — Celeste A Roney
(74) *Attorney, Agent, or Firm* — Edwin S. Flores; Chalker Flores, LLP

(57) ABSTRACT

The present invention includes a composition and method for treating a glioblastoma in a human or animal subject comprising the steps of: identifying the human or animal subject in need of treatment of a glioblastoma, wherein the human or animal is no longer responsive to at least one of chemotherapy, surgery, or radiation therapy; and administering to the human or animal subject a therapeutically effective amount of a composition comprising: an amount of a curcumin or curcuminoids in one or more liposomes, or curcumin or curcuminoids and empty liposomes and administered prior to, concomitantly, or after administration of the curcumin or curcuminoids, that is effective for treating the glioblastoma, wherein the liposomal curcumin or curcuminoids, or empty liposomes, eliminate the QT prolongation caused by the curcumin or curcuminoids; and at least one chemotherapeutic agent that is synergistic with curcumin to treat the glioblastoma.

7 Claims, No Drawings

(56) References Cited

OTHER PUBLICATIONS

Schiffer, D., et al., "Glioblastoma cancer stem cells: Basis for a functional hypothesis," Stem Cell Discovery, Jun. 10, 2012, vol. 2, No. 3, pp. 122-131.
Sehedic, D., et al., "Nanomedicine to overcome radioresistance in glioblastoma stem-like cells and surviving clones," Trends in Pharmacological Sciences, 2015, pp. 1-17.
Senft, C., et al., "The nontoxic natural compound Curcumin exerts anti-proliferative, anti-migratory, and anti-invasive properties against maignant gliomas," BMC Cancer, Sep. 14, 2010, vol. 10:491, pp. 1-8.
Shahar, T., et al., "The impact of enrollment in clinical trials on survival of patients with glioblastoma," Journal of Clinical Neuroscience, vol. 19, Apr. 4, 2012, pp. 1530-1534.
Sharma, R., et al., "Phase I Clinical Trial of Oral Curcumin: Biomarkers of Systemic Activity and Compliance," vol. 10, Oct. 15, 2004, pp. 6847-6854.
Sordillo, P., et al., "Curcumin Suppression of Cytokine Release and Cyokine Storm. A Potential Therapy for Patients with Ebola and Other Severe Viral Infections," In Vivo, vol. 29, Nov. 13, 2014, pp. 1-4.
Sordillo, P., et al., "Curcumin and Cancer Stem Cells: Curcumin Has Asymmetrical Effects on Cancer and Normal Stem Cells," Anticancer Research, vol. 35, Oct. 24, 2014, pp. 599-614.
Storka, A., et al., "Safety, tolerability and pharmacokinetics of *Liposomal curcumin* (Lipocurc) in healthy humans," International Journal of Clinical Pharmacology and Therapeutics, Aug. 3, 2014, pp. 1-12.
Stupp, R., et al., "Radiotherapy plus Concomitant and Adjuvant Temozolomide for Glioblastoma," The New England Journal of Medicine, 352:10, Mar. 10, 2015, pp. 987-996.
Stupp, R., et al., "Effects of radiotherapy with concomitant and adjuvant temozolomide versus radiotherapy alone on survival in glioblastoma in a randomised phase III study: 5-year analysis of the EORTC-NCIC trial," Lancet Oncol., vol. 10, Mar. 9, 2009, pp. 459-466.
Subramaniam, D., et al., "Curcumin Induces Cell Death in Esophageal Cancer Cells through Modulating Notch Signaling," PLoS ONE, vol. 7, Issue 2, Feb. 2012, pp. 1-11.
Taal, W., "Chemotherapy in Glioma," Lancet Oncol., vol. 15(9) Aug. 2014, pp. 943-953.
Tang, C., et al., "Gene mutation profiling of primary glioblastoma through multiple tumor biopsy guided by 1H-magnetic resonance spectroscopy," vol. 8:5, May 15, 2015, Int. J. Clin. Esp. Pathol., pp. 5327-5335.
Taylor, T., et al., "Targeting EGFR for Treatment of Glioblastoma: Molecular Basis to Overcome Resistance," Curr. Cancern Drug Targets, vol. 12(3), Mar. 2012, pp. 197-209.
Virk, S., et al., "Identification of Variants in Primary and Recurrent Glioblastoma Using a Cancer-Specific Gene Panel and Whole Exome Sequencing," PLoS ONE, May 7, 2015, pp. 1-10.
Woo, Moon-Sook, et al., "Curcumin suppresses phorbol ester-induced matrix metalloproteinase-9 expression by inhibiting the PKC to MAPK signaling pathways in human astroglioma cells," Biochemical and Biophysical Research Communications, 335, Aug. 9, 2005, pp. 1017-1025.
Wu, H., et al., "Induction of microRNA-146a is involved in curcumin-mediated enhancement of temozolomide cytotoxicity against human glioblastoma," Molecular Medicine Reports, vol. 12, Jun. 29, 2015, pp. 5461-5466.
Yin, H., et al., "Curcumin sensitizes glioblastoma to temozolomide by simultaneously generating ROS and disrupting AKT/mTOR signaling," Oncology Reports, vol. 32, Jul. 2, 2014, pp. 1610-1616.
Zanotto-Filho, A., et al., "The curry spice curcumin selectively inhibits cancer cells growth in vitro and in reclinical model of glioblastoma," Journal of Nutritional Biochemistry, vol. 23, 2012, pp. 591-601.
Zanotto-Filho, A., et al., "Curcumin-loaded lipid-core nanocasules as a strategy to improve pharmacological efficacy of curcumin in glioma treatment," European Journal of Pharmaceutics and Biopharmaceutics, vol. 83, Feb. 2013, pp. 156-167.
Zhuang, W., et al., "Curcumin Promotes differentiation of glioma-initiating cells by inducing autophagy," Cancer Science, vol. 103:4, Apr. 2012, pp. 684-690.
Aggarwal, et al., "Anticancer Potential of Curcumin: Preclinical and Clinical Studies," Anticancer Research, vol. 23, 2003, pp. 363-398.
Alexandrow, M.G., et al., "Curcumin: a novel Stat3 pathway inhibitor for chemoprevention of lung cancer," Eur. J. Cancer Prev. 21(5), Sep. 2012, pp. 407-412.
Almanaa, T.N., et al., "Effects of curcumin on stem-like cells in human esophageal squamous carcinoma cell lines," BMC Complementary and Alternative Medicine, vol. 12:195, Oct. 24, 2012, 15 pp.
Anggakusma, C., et al., "Turmeric curcumin inhibits entry of all hepatitis C virus genotypes into human liver cells," Gut, vol. 63(7), Jul. 31, 2013, pp. 1137-1149.
Aoki, H., et al., "Evidence that curcumin suppresses the growth of malignant gliomas in vitro and in vivo through induction of autophagy: role of Akt and extracellular signal-regulated kinase signaling pathways," Mol. Pharmacol., vol. 72:1, Mar. 2007, pp. 29-39.
Arif, S.H., et al., "EGFR and PTEN gene mutation status in glioblastoma patients and their prognostic impact on patient's survival," J. Carcinog. Mutagen, vol. 6:2, Mar. 24, 2015, 7 pp.
Beier, D., et al., "Chemoresistance of glioblastoma cancer stem cells—much more complex than expected," Mol. Cancer, vol. 10:1 28, Oct. 11, 2011, 11 pp.
Belkaid, A., et al., "Silencing of the human microsomal glucose-6-phosphate translocase induces glioma cell death: potential new anticancer target for curcumin," FEBS Letters 580, May 31, 2006, pp. 3746-3752.
Bisht, S., et al., "Systemic Administration of polymeric nanoparticle-encapsulated curcumin (NanoCurc) blocks tumor growth and metastases in preclinical models of pancreatic cancer," Mol. Cancer Ther., vol. 9(8), Aug. 2010, pp. 2255-2264.
Bleau, A.M., et al., "PTEN/PI3K/Akt pathway regulates the side population phenotype and ABCG2 activity in glioma tumor stem-like cells," Cell Stem Cell, vol. 4, Mar. 5, 2009, pp. 226-235.
Brown, P.D., et al, "A prospective study of quality of life in adults with newly diagnosed high-grade gliomas: the impact of the extent of resection on quality of life and survival," Neurosurgery vol. 57(3):495-504; discussion 495-504, 2005.
Castillo, S.S., et al., "Reactive nitrogen and oxygen species activate different sphingomyelinases to induce apoptosis in airway epithelial cells," Exp. Cell Res., vol. 313, Apr. 1, 2007, pp. 2680-2686.
Chaichana, K.L., et al, "Establishing percent resection and residual volume thresholds affecting survival and recurrence for patients with newly diagnosed intracranial glioblastoma," Neuro. Oncol., vol. 16 Jul. 29, 2013, pp. 113-122.
Chandran, B., et al., "A randomized, pilot study to assess the efficacy and safety of curcumin in patients with active rheumatoid arthritis," Phytother. Res., vol. 26(11), Jan. 23, 2012, 1719:1725.
Cheng, A.L., et al., "Phase I clinical trial of curcumin, a chemopreventive agent, in patients with high-risk or pre-malignant lesions," Anticancer Res., vol. 21(4B), May 2, 2001, pp. 2895-2900.
Chinot, O.L., et al, "Bevacizumab plus radiotherapy—temozolomide for newly diagnosed glioblastoma," N. Engl. J. Med., vol. 370, Feb. 24, 2014, pp. 709-722.
Chiu, S.S., et al., "Differential distribution of intravenous curcumin formulations in the rat brain," Anticancer Res., vol. 31(3), Feb. 24, 2011, pp. 907-911.
Choi, B.H., et al., "p21Waf1/Cip1 expression by curcumin in U-87MG human glioma cells: role of early growth response-1 expression," Cancer Res., vol. 68(5), Mar. 1, 2008, pp. 1369-1377.
Cohen, M.H., et al., "Food and drug administration drug approval summary: temozolomide plus radiation therapy for the treatment of newly diagnosed glioblastoma multiforme," Clin. Cancer Res., vol. 11, Oct. 1, 2005, pp. 5767-6771.
Darefsky, A.S., et al., "Adult glioblastoma multiforme survival in the temozolomide era: a population-based analysis of surveillance, epidemiology, and end results registries," Cancer vol. 118, Aug. 31, 2011, pp. 2163-2172.

(56) References Cited

OTHER PUBLICATIONS

Dhandapani, K.M., et al., "Curcumin suppresses growth and chemoresistance of human glioblastoma cells via AP-1 and NFkappaB transcription factors," J. Neurochem., vol. 102, Jan. 31, 2007, pp. 522-538.
Elamin, M.H., et al., "Curcumin inhibits the Sonic Hedgehog signaling pathway and triggers apoptosis in medulloblastoma cells," Mol. Carcinog., vol. 49, Dec. 18, 2009, pp. 302-314.
Fong, D., et al., "Curcumin inhibits the side population (SP) phenotype of the rat C6 glioma cell line: towards targeting of cancer stem cells with phytochemicals," Cancer Letters 293(1), Jul. 1, 2010, pp. 65-72.
Ganta, S., et al., "Coadministration of paclitaxel and curcumin in nanoemulsion formulations to overcome multidrug resistance in tumor cells," Mol. Pharm., vol. 6, Mar. 11, 2009, pp. 928-939.
Gilbert, M.R., et al, "A randomized trial of bevacizumab for newly diagnosed glioblastoma," N. Engl. J. Med., vol. 370, No. 8, Feb. 20, 2014, pp. 699-708.
Giussani, P., et al., "Glucosylceramide synthase protects glioblastoma cells against autophagic and apoptotic death induced by temozolomide and Paclitaxel," Cancer Invest., vol. 30, Jan. 31, 2012, pp. 27-37.
Grammatikos, G., et al., "Overexpression of acid sphingomyelinase sensitizes glioma cells to chemotherapy," Antioxid Redox Signal, vol. 9:9, Apr. 3, 2007, pp. 1449-1456.
Hara, S., et al, "p53-Independent ceramide formation in human glioma cells during gamma-radiation-induced apoptosis," Cell Death Differ., vol. 11, Apr. 16, 2004, pp. 853-861.
Sordillo, L.A., et al., "Curcumin for the Treatment of Gioblastoma," Anticancer Research, vol. 35, No. 12, Dec. 2015, pp. 6373-6378.
Hossain, MM, et al., "Synergistic anti-cancer mechanisms of curcumin and paclitaxel for growth inhibition of human brain tumor stem cells and LN18 and U138MG cells," Neurochem Int., 61(7), Dec. 2012, pp. 1102-1111.
Jain, RK, et al., "Angiogenesis in brain tumours," Nat. Rev. Neurosci., vol. 8, Aug. 2007, pp. 610-622.
Karmaker, S., et al., "Curcumin activated both receptor mediated and mitochondria-mediated proteolytic pathways for apoptosis in human glioblastoma T98G cells," Neurosci. Letters 407, Aug. 4, 2006, pp. 53-58.
Kim, So-Young, et al., "Curcumin is a potent broad spectrum inhibitor of matrix metalloproteinase gene expression in human astroglioma cells," Biochem. Biophys. Res. Commun. 337, Sep. 21, 2005, pp. 510-516.
Langone, P., et al., "Coupling to a glioblastoma-directed antibody potentiates antitumor activity of curcumin," International Journal of Cancer, 135, Oct. 1, 2013, pp. 710-719.
Leow, Pay-Chin, et al., "Antitumor activity of natural compounds, curcumin and PKF118-310, as Wnt/B-catenin antagonists against human osteosarcoma cells," Invest New Drugs, vol. 28, Sep. 3, 2009, pp. 766-782.
Li, X., et al., "Instrinsic Resistance of Tumorigenic Breast Cancer Cells to Chemotherapy," vol. 100:9, May 7, 2008, pp. 672-679.
Lim, K.J., et al., "A plymeric nanoparticle formulation of curcumin inhibits growth, clonogenicity and stem-like fraction in malignant brain tumors," Cancer Biology & Therapy, vol. 11:5, Mar. 1, 2011, pp. 464-473.
Manago, A., et al., "Pseudomonas aeruginosa Pyocyanin Induces neutrophil Death via Mitochondrial Reactive Oxygen Species and Mitochondrial Acid Sphingomyelinase," Antioxidants & Redox Signaling, vol. 22:13, Feb. 9, 2015.
Mason, W. P., et al., "Drug Insight: temozolomide as a treatment for malignant glioma—impact of a recent trial," Nature Clinical Practice Neurology, vol. 1:2, Dec. 2005, pp. 88-95.
McGirt, M. J., et al., "Association of Surgically Acquired Motor and Language Deficits on Overall Survival After Resection of Glioblastoma Multiforme," Neurosurgery, vol. 65, No. 3, Sep. 2009, pp. 463-470.
Extended European Search Report for 16188460.6 dated Nov. 21, 2016, 12 pp.
Dhandapani, M. K., et al., "Curcumin suppresses growth and chemoresistance of human glioblastoma cells via AP-1 and NFκB transcription factors." Journal of Neurochemistry, Jul. 2007, vol. 102, No, 2, pp. 522-538.
Ramachandran, C., et al., "Potentiation of etoposide and temozolomide cytotoxicity by curcumin and turmeric force™ in brain tumor cell lines." Journal of Complementary and Integrative Medicine, 2012, vol. 9, No. 1, Article 20.
Baran, Y., et al., "Alterations of Ceramide/Sphingosine 1-Phosphate Rheostat Involved in the Regulation of Resistance to Imatinib-induced Apoptosis in K562 Human Chronic Myeloid Leukemia Cells," The Journal of Biological Chemistry, vol. 282, No. 15, Apr. 13, 2007, pp. 10922-10934.
International Search Report and Written Opinion of PCT/US2017/018889 by the Korean Intellectual Property Office dated May 22, 2017, 13 pp.
Payne, Ania W., et al., "Ceramide Kinase Promotes Tumor Cell Survival and Mammary Tumor Recurrence," Cancer Research, Tumor and Stern Cell Biology, vol. 74(21), Nov. 1, 2014, pp. 6352-6363.
Ponnusamy, S., et al., "Sphingolipids and Cancer: Ceramide and sphingosine-1-phosphate in the regulation of cell death and drug resistance," Future Oncol., vol. 6(10, Oct. 2010, pp. 1603-1624.
Sordillo, L. A., et al., "Sphingosine Kinase Inhibitors as Maintenance Therapy for Glioblastoma After Ceramide-Induced Response," Anticancer Research, vol. 36, Apr. 13, 2016, pp. 2085-2096.
Desai, et al., "Cytotoxicity and Apoptosis Enhancement in Brain Tumor Cells Upon Coadministration of Paclitaxel and Ceramide in Nanoemulsion Formulations," Pharmaceutical Nanotechnology, vol. 97:7, Jul. 2008.
Dhule, S., et al., "The Combined Effect of Encapsulating Curcumin and C6 Ceramide in Liposomal Nanoparticles against Osteosarcoma," Molecular Pharmaceutics, 2014, vol. 11, pp. 417-427.
Gao, Y., et al, "Sphingosine kinase 1 as an anticancer therapeutic target," Drug Des. Devel. Ther., Jun. 23, 2015, vol. 9, pp. 3239-3245.
Liu, Jiawang, et al., "A review of ceramide analogs as potential anticancer agents," Future Med. Chem., Aug. 2013, vol. 5(12), pp. 1405-1421.
Saddoughi, S., et al., "Diverse Functions of Ceramide in Cancer Cell Death and Proliferation," Advances in Cancer Research, vol. 117, 2013, pp. 37-58.
Estrada-Bernal, et al., "Induction of brain tumor stem cell apoptosis by FTY720: a potential therapeutic agent for glioblastoma," Nuero-Oncology, Feb. 20, 2012, vol. 14(4), pp. 405-415.
Zhang, L., et al., "FTY720 induces autophagy-related apoptosis and necroptosis in human Glioblastoma cells," Toxicology Letters 236, May 1, 2015, pp. 43-59.

* cited by examiner

TREATMENT FOR GLIOBLASTOMA

CROSS-REFERENCE TO RELATED APPLICATIONS

This application claims priority to U.S. Provisional Application Ser. No. 62/220,635 filed Sep. 18, 2015, the entire contents of which are incorporated herein by reference.

TECHNICAL FIELD OF THE INVENTION

The present invention relates in general to the field of cancer treatments, and more particularly, to compositions and methods for treating glioblastomas.

STATEMENT OF FEDERALLY FUNDED RESEARCH

None.

BACKGROUND OF THE INVENTION

Without limiting the scope of the invention, its background is described in connection with treatments for glioblastoma.

One such method of treatment is taught in U.S. Pat. No. 8,945,563, issued to Auf Der Maur, et al., entitled "Method for treating glioblastoma using antibodies binding to the extracellular domain of the receptor tyrosine kinase ALK." Briefly, these inventors are said to teach an antibody specific for human ALK (Anaplastic Lymphoma Kinase), in particular a scFv, a nucleic acid sequence encoding it, its production and use as a pharmaceutical, for diagnostic purposes, and the local treatment of glioblastoma.

Another method is taught in U.S. Pat. No. 8,518,698, issued to Sugaya, et al., entitled "Method of promoting apoptosis of glioblastoma tumor cells." Briefly, these inventors are said to teach a method of promoting apoptosis of human glioblastoma multiforme (GBM) tumor cells. The method is said to comprise: isolating GBM tumor cells from a human brain biopsy specimen, isolating human neural stem cells (HNSCs) from the biopsy specimen, transforming the isolated HNSCs with an operative PEX gene, and exposing GBM tumor cells to the transformed HNSCs to promote apoptosis of the tumor cells mediated by the expressed PEX gene.

Yet another method is taught in U.S. Pat. No. 7,931,922, issued to Newmark, et al., entitled "Methods for treating glioblastoma with herbal compositions". Briefly, these inventors are said to teach methods for treating glioblastoma, by administration of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry. It is said that this composition modulates gene expression of genes selected from the group consisting of interleukin-1α, interleukin-1β, heme oxygenase 1, aldo-keto reductase family 1 member C2, colony stimulating factor 3, leukemia inhibitory factor, and heat shock 70 kDa protein.

SUMMARY OF THE INVENTION

One embodiment of the present invention includes a method for treating a glioblastoma in a human or animal subject comprising the steps of: identifying the human or animal subject in need of treatment of a glioblastoma, wherein the human or animal is no longer responsive to at least one of chemotherapy, surgery, or radiation therapy; and administering to the human or animal subject a therapeutically effective amount of a composition comprising: an amount of a curcumin or curcuminoids in one or more liposomes, or curcumin or curcuminoids and empty liposomes, and administered prior to, concomitantly, or after administration of the curcumin or curcuminoids, that is effective for treating the glioblastoma, wherein the liposomal curcumin or curcuminoids, or empty liposomes, eliminate the QT prolongation caused by the curcumin or curcuminoids; and at least one chemotherapeutic agent that is synergistic with curcumin to treat the glioblastoma. In one aspect, the chemotherapeutic agent is selected from at least one of temozolomide, etoposide, doxorubicin, cisplatin, paclitaxel, carmustine, lomustine, ceramide and phosphorylcholine. In another aspect, the QT prolongation is LQTS. In another aspect, the liposomal curcumin or curcuminoids, or empty liposomes are provided intravenously. In another aspect, the composition increases ceramide production of the glioblastoma cell. In another aspect, the composition increases phosphorylcholine production of the glioblastoma cell. In another aspect, the glioblastoma cells are sensitized to an agent to which they have become refractory as a result of increased ceramide production in the glioblastoma cell. In another aspect, the glioblastoma cells are sensitized to an agent to which they have become refractory as a result of increased phosphorylcholine production in the glioblastoma cell.

Another embodiment of the present invention includes a method for treating a glioblastoma in a human or animal subject comprising the steps of: identifying the human or animal subject in need of treatment of a glioblastoma, wherein the human or animal is no longer responsive to at least one of chemotherapy, surgery, or radiation therapy; and administering to the human or animal subject a therapeutically effective amount of a composition comprising: an amount of a curcumin or curcuminoids in one or more liposomes, or curcumin or curcuminoids and empty liposomes, and administered prior to, concomitantly, or after administration of the curcumin or curcuminoids, that is effective for treating the glioblastoma, wherein the liposomal curcumin or curcuminoids, or empty liposomes, eliminate the QT prolongation caused by the curcumin or curcuminoids; and at least one chemotherapeutic agent that is synergistic with curcumin to treat the glioblastoma, selected from at least one of temozolomide, etoposide, doxorubicin, cisplatin, paclitaxel, carmustine, lomustine, ceramide and phosphorylcholine. In one aspect, the QT prolongation is LQTS. In another aspect, the liposomal curcumin or curcuminoids, or empty liposomes are provided intravenously. In another aspect, the composition increases ceramide production of the glioblastoma cell. In another aspect, the composition increases phosphorylcholine production of the glioblastoma cell. In another aspect, the glioblastoma cells are sensitized to an agent to which they have become refractory as a result of increased ceramide production in the glioblastoma cell. In another aspect, the glioblastoma cells are sensitized to an agent to which they have become refractory as a result of increased phosphorylcholine production in the glioblastoma cell.

Yet another embodiment of the present invention includes a method of determining the effectiveness of a candidate drug that is a chemotherapeutic agent that sensitizes or synergizes with curcumin to treat the glioblastoma, the method comprising: measuring the effect of a candidate agent on a glioblastoma cell; administering the candidate drug to a first subset of glioblastoma cells, and a combination of the candidate drug with curcumin to a second subset of glioblastoma cells; and determining if the curcumin sensitizes or synergizes the glioblastoma cells to the candidate agent in the first versus the second subset of glioblastoma cells. In one aspect, the method further comprises the step of determining if the candidate drug increases ceramide production of the glioblastoma cell. In another aspect, the method further comprises the step of determining if the candidate drug increases phosphorylcholine production of the glioblastoma cell. In another aspect, the method further comprises the step of determining if the glioblastoma cells are sensitized to an agent to which they have become refractory as a result of increased ceramide production in the glioblastoma cell. In another aspect, the method further comprises the step of determining if the glioblastoma cells are sensitized to an agent to which they have become refractory as a result of increased phosphorylcholine production in the glioblastoma cell.

Another embodiment of the present invention includes a composition comprising an amount of a curcumin or curcuminoids in one or more liposomes, or curcumin or curcuminoids and empty liposomes and administered prior to, concomitantly, or after administration of the curcumin or curcuminoids, that is effective for treating the glioblastoma, wherein the liposomal curcumin or curcuminoids, or empty liposomes, eliminate the QT prolongation caused by the curcumin or curcuminoids; and at least one chemotherapeutic agent that is synergistic with curcumin to treat the glioblastoma.

Another embodiment of the present invention includes a composition consisting essentially of an amount of a curcumin or curcuminoids in one or more liposomes, or curcumin or curcuminoids and empty liposomes and administered prior to, concomitantly, or after administration of the curcumin or curcuminoids, that is effective for treating the glioblastoma, wherein the liposomal curcumin or curcuminoids, or empty liposomes, eliminate the QT prolongation caused by the curcumin or curcuminoids; and at least one chemotherapeutic agent that is synergistic with curcumin to treat the glioblastoma.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Glioblastoma multiforme is a highly aggressive primary cancer of the brain associated with a poor prognosis. Modest increases in survival can sometimes be achieved with the use of temozolomide and radiation therapy after surgery, but second line therapy after recurrence has limited efficacy. Curcumin has demonstrated promising results against this cancer in experimental models. The reported activity of curcumin against cancer stem cells, a major cause of glioblastoma resistance to therapy, and its ability to augment the apoptotic effects of ceramides, suggests a synergistic effect with cytotoxic chemotherapy agents currently used in second-line therapy, such as lomustine.

Glioblastoma (glioblastoma multiforme, (GBM)) is a highly malignant (grade IV) tumor arising from astrocytes. About 15 percent of all primary brain tumors are GBM. GBM may arise de novo or, occasionally, from a low-grade astrocytoma. Genetic abnormalities are common (1-4). Median survival with treatment is 15 months, with a two-year survival of less than 25%. Survival without treatment is usually only a few months (5-8). Frequent presenting signs include headaches, nausea, seizures, blurred vision, vomiting, and personality changes. Standard treatment is a combination of surgery, radiotherapy, and chemotherapy. The effectiveness of surgery is limited by the difficulty of complete tumor resection and the presence of residual tumor cells (9-11). If surgical ablation is not an option due to tumor size, tumor location, or very poor patient performance status, a combination of radiation and chemotherapy is used.

Standard Chemotherapy for Glioblastoma. Temozolomide (TMZ) is an oral alkylating agent, which is an imidazotetrazine derivative of dacarbazine. TMZ crosses the blood-brain barrier and is, in combination with radiation, the most frequently used first-line treatment given following surgery (12-15). A randomized trial of radiation therapy plus TMZ showed a modest increase in patient median survival with the addition of TMZ to radiotherapy. Median survival with this combination is 14.6 months compared to 12.1 months with radiation therapy alone (16-18). Two other agents, bevacizumab (which suppresses angiogenesis), and lomustine (CCNU) have frequently been used as second-line therapy (19-23). Lomustine is a lipid-soluble, alkylating nitrosourea, which also crosses the blood-brain barrier (21-25). However, treatment with these agents results in only minor increases in survival, and overall patient survival rates remain low with a 5 year survival of less than 10% at five years after diagnosis (18, 26). Due to the highly resistant and aggressive nature of GBM, new treatments are needed.

Curcumin. Curcumin (diferuloylmethane) is the principal curcuminoid of turmeric, the Indian spice derived from the plant *Curcuma longa linn*. Curcumin absorbs light with a wavelength maximum at approximately 420 nm, thus giving turmeric its yellow color. Curcumin has been shown to have anti-oxidant, anti-infective and anti-cancer effects, and its use is being investigated in diseases as diverse as diabetes (27), Alzheimer's disease (28), hepatitis (29) and rheumatoid arthritis (30). When orally administered, it is non-toxic and safe (31-35). Curcumin has numerous mechanisms of action, including suppressing pro-inflammatory cytokines such as TNFα, IL1, IL6, IL8, and affects multiple signaling pathways including Wnt, notch, MAKP, hedgehog and JAK/STAT (36-41). Curcumin is highly lipophilic, and crosses the blood-brain barrier (42, 43).

Curcumin and GBM. The potential benefits of curcumin as a treatment for GBM have been studied by numerous groups (44-49). Aoki et al showed that curcumin induced autophagy by suppression of the Akt/mTOR/p70S6K and activation of the ERK1/2 pathways in U87-MG and U373-MG human malignant glioma cells harboring a PTEN mutation. Similar results were seen in KBM-5 human leukemia cells (50). Choi et al reported that curcumin activates p21 in U87-MG human GBM cells via ERK and JNK signaling (51). Senft et al studied human primary and recurrent GBM cell lines, and showed that curcumin reduced cell growth, inhibited migration and decreased invasiveness due to its inhibition of the JAK/STAT3 pathway (52). Similarly, Dhandapani et al showed that curcumin enhanced cell death by reducing the activity of AP-1 and NFκB binding in human and rat glioma cell lines (53). Zanotto-Filho et al showed that, in the C6 implant rat glioma model, curcumin caused reduction in brain tumor volume (54). Perry et al showed that curcumin can suppress growth of human glioma U87 cells xenografted into athymic mice (55).

Curcumin's effects on GBM stem cells may also be important. Beier et al have shown that detoxifying proteins such as O6-methylguanine-DNA-methyltransferase (MGMT) may confer the intrinsic resistance of cancer stem cells to alkylating agents (56). Other researchers have also suggested a key role for stem cells in GBM formation and resistance to alkylating agent therapy (57, 58). Fong et al studied rat C6 glioma cells, and showed that curcumin may have the potential to target cancer stem cells (59). Zhuang et al found that curcumin induced differentiation of glioma-initiating cells and inhibited their growth via autophagy (60).

Curcumin: Alternate Delivery Mechanisms. Recently, new mechanisms have emerged, and engendered methods of improving the efficacy of curcumin (61-65). These methods may prove superior because of their ability to deliver greater doses of curcumin to the tumor. Nano-sized capsules of curcumin have been used as a treatment of GBM cells. Lim et al have shown that curcumin nanoparticles can slow GBM growth through the inhibition of cell proliferation and a reduction in stem-like tumor cells (66). Langone et al have shown that curcumin coupled to a monoclonal antibody caused a 120-fold increase in the death of human GBM cells in culture compared to curcumin alone. In addition, mice implanted with GBM cells had an extended survival time and a reduction in the size of the brain tumor mass with this treatment (67).

Rationale for Combination therapy. The present invention includes an optimal method of using curcumin, not as a single agent, but rather in combination with cytotoxic chemotherapy. Ramachandran et al have shown that curcumin could be used to increase the therapeutic potential of TMZ or of etoposide in brain tumor cell lines (68). Yin et al investigated the use of a combination of curcumin and TMZ in U87MG GBM cell lines and in xenograft mouse models, and found that curcumin enhanced the effects of TMZ by generating reactive oxygen species production, and by suppressing phosphorylated AKT and mTOR, thus causing cell death (69). Zanotto-Filho et al showed that curcumin could increase the cytotoxic effects of doxorubicin and cisplatin on GBM cells (70). Wu et al showed curcumin enhanced TMZ cytotoxicity of human GBM cells (71). It has been reported that curcumin and paclitaxel act synergistically with much greater activity than seen with each individual agent in increasing the Bax:Bcl-2 ratio, increasing cytochrome C, reducing angiogenesis and causing apoptosis of HBTSC, LN18 and U138MG cells (72).

These results suggest that the use of curcumin should be investigated in clinical trials of patients with GBM, ideally as a second line therapy after failure of radiation therapy and TMZ, and that the optimal method for using curcumin in this setting may be in combination with an established cytotoxic chemotherapy agent with activity against GBM such as carmustine or lomustine. As noted, it appears that a major reason for the very limited efficacy of alkylating agents in established tumors is the resistance of GBM stem cells to therapy. The inventors' previous work shows that curcumin may be effective in reducing or eliminating the population of cancer stem cells, either by causing their apoptosis or their differentiation (73-76), while conventional chemotherapy alone is ineffective against stem cells, resulting in tumor recurrence even following initial response (77). Further, curcumin may also increase the activity of cytotoxic chemotherapy against mature tumor cells. Curcumin has been shown to enhance ceramide production by increasing the activity of enzyme ceramide synthase (78). It has been suggested that the progression of GBM is caused by a decrease in ceramide levels (79). Increased activity of glucosylceramide synthase, an enzyme that causes a decrease in ceramides, has been associated with GBM progression and resistance to TMZ (80). In contrast, acid sphingomyelinase, which hydrolyzes sphingomyelin to ceramide and phosphorylcholine, has been shown to sensitize glioma cell lines to chemotherapy or radiation therapy (81, 82). The combination of curcumin and chemotherapy has also been shown to have a synergistic effect on the generation of reactive oxygen species (ROS) in GBM cell lines and in mouse xenografts (69). This may be additional mechanism by which GBM cell destruction might be enhanced, since ROS are known to increase acid sphingomyelinase activity and, in consequence, ceramide levels (83-85).

However, it has been found that using the liposomal curcumin, curcumin and empty liposomes and a second chemotherapeutic agent that synergizes with curcumin, for example, by increasing ceramide levels, the present invention can be used to treat glioblastoma patients that have become resistant to first-line therapies. Further, the present inventors have found that the liposomal curcumin and/or curcumin and empty liposomes fail to trigger QT interval prolongation, which is a critical reason that curcumin or curcuminoids alone cannot be used intravenously. As such, the present invention opens a new path for treatment of glioblastoma heretofore unknown.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1 Virk S M, Gibson R M, Quinones-Mateu M E and Barnholtz-Sloan J S: Identification of variants in primary and recurrent glioblastoma using a cancer-specific gene panel and whole exome sequencing. PLos ONE 10(5): e0124174, 2015.
2 Tang C, Guo J, Chen H, Yao C, Zhuang D, Wang Y, Tang W, Ren G, Wu J, Mao Y and Zhou L: Gene mutation profiling of primary glioblastoma through multiple tumor biopsy guided by 1H-magnetic resonance spectroscopy. Int J Clin Exp Pathol 8(5): 5327-5335, 2015.
3 Taylor T, Fumari F and Cavenee W: Targeting EGFR for treatment of glioblastoma: molecular basis to overcome resistance. Curr Cancer Drug Targets 12(3): 197-209, 2012.
4 Arif S H, Pandith A A, Bhat A R, Ramzan A U, Malik N K, Chibber S S, Wani A A, Tabasum R and Kirmani A: EGFR and PTEN gene mutation status in glioblastoma patients and their prognostic impact on patient's survival. J Carcinog Mutagen 6:218, 2015.
5 American Brain Tumor Association. http://www.abta.org/brain-tumor-information/types-of-tumors/glioblastoma.html
6 National Brain Tumor Society. http://braintumor.org/brain-tumor-information/understanding-brain-tumors/tumor-types/
7 Shahar T, Nossek E, Steinberg D M, Rozovski U, Blumenthal D T, Bokstein F et al: The impact of enrollment in clinical trials on survival of patients with glioblastoma. J Clin Neurosci 19: 1530-1534, 2012.
8 Park J K, Hodges T, Arko L, Shen M, Iacono D D, McNabb A, Bailey N O, Kreisi T N, Iwamoto F M, Sul J, Auh S, Park G E, Fine H A, McL.Black P: Scale to predict survival after surgery for recurrent glioblastoma multiforme. J Clinical Oncology 28(24): 3838-3843, 2010.
9 Chaichana K L. Jusue-Torres I. Navarro-Ramirez R. Raza S M. Pascual-Gallego M. Ibrahim A. Hernandez-Hermann M. Gomez L. Ye X. Weingart J D., et al: Establishing percent resection and residual volume thresholds affecting survival and recurrence for patients with newly diagnosed intracranial glioblastoma. Neuro Oncol 16: 113-122, 2013.
10 McGirt M J, Mukherjee D, Chaichana K L, Than K D, Weingart J D and Quinones-Hinojosa A: Association of 10 surgically acquired motor and language deficits on overall survival after resection of glioblastoma multiforme. Neurosurgery 65(3): 463-469; discussion 469-470, 2009.

11 Brown P D, Maurer M J, Rummans T A, et al: A prospective study of quality of life in adults with newly diagnosed high-grade gliomas: the impact of the extent of resection on quality of life and survival. Neurosurgery 57(3):495-504; discussion 495-504, 2005.

12 Mason W P and Cairncross J G: Drug insight: temozolomide as a treatment for malignant glioma—impact of a recent trial. Nat Clin Pract Neurol. 1: 88-95, 2005.

13 Nagasawa D T, Chow F, Yew A, Kim W, Cremer N and Yang I: Temozolomide and other potential agents for the treatment of glioblastoma multiforme. Neurosurg Clin N Am 23: 307-322, 2012.

14 Cohen M H, Johnson J R and Pazdur R: Food and drug administration drug approval summary: temozolomide plus radiation therapy for the treatment of newly diagnosed glioblastoma multiforme. Clin Cancer Res 11: 6767-6771, 2005.

15 Rosso L, Brock C S, Gallo J M, Saleem A, Price P M, Turkheimer F E and Aboagye E O: A new model for prediction of drug distribution in tumor and normal tissues: Pharmacokinetics of temozolomide in glioma patients. Cancer Res 69: 120-127, 2009.

16 Stupp R, Mason W P, van den Bent M J, et al: Radiotherapy plus concomitant and adjuvant temozolomide for glioblastoma. N Eng J Med 352:987-96, 2005.

17 Stupp R, Hegi M E, Mason W P, et al. Effects of radiotherapy with concomitant and adjuvant temozolomide versus radiotherapy alone on survival in glioblastoma in a randomised phase III study: 5-year analysis of the EORTC-NCIC trial. Lancet Oncol 10(5): 459-66, 2009.

18 Darefsky A S, King J T Jr. and Dubrow R. Adult glioblastoma multiforme survival in the temozolomide era: a population-based analysis of surveillance, epidemiology, and end results registries. Cancer 118: 2163-2172, 2011.

19 Lund E L, Spang-Thomsen M, Skovgaard-Poulsen H and Kristjansen P E: Tumor angiogenesis—a new therapeutic target in gliomas. Acta Neurol Scand 97: 52-62, 1998.

20 Jain R K, di Tomaso E, Duda D G, Loeffler J S, Sorensen A G and Batchelor T T: Angiogenesis in brain tumours. Nat Rev Neurosci 8: 610-622, 2007.

21 Taal W, OOsterkamp H, Walenkamp A, et al: Single-agent bevacizumab or lomustine versus a combination of bevacizumab plus lomustine in patients with recurrent glioblastoma (BELOB trial): a randomised controlled phase 2 trial. Lancet Oncology 15: 943-953, 2014.

22 Gilbert M R et al: A randomized trial of bevacizumab for newly diagnosed glioblastoma. N Engl J Med 370: 699-708, 2014.

23 Chinot O L et al: Bevacizumab plus radiotherapy—temozolomide for newly diagnosed glioblastoma. N Engl J Med 370: 709-722, 2014.

24 Schabel F M Jr: Nitrosoureas: a review of experimental antitumor activity. Cancer Treat Rep 60(6): 665-698, 1976.

25 Agarwal S, Chadha D and Mehrotra R: Molecular modeling and spectroscopic studies of semustine binding with DNA and its comparison with lomustine-DNA adduct formation. J Biomol Struct Dyn 33(8): 1653-1668, 2015.

26 Patel M A, Kim J E, Ruzevick J, Li G and Lim M: The future of glioblastoma therapy: synergism of standard of care and immunotherapy. Cancers 6: 1953-1985, 2014.

27 Meng B, Li J and Cao H: Antioxidant and antiinflammatory activities of curcumin on diabetes mellitus and its complications. Curr Pharm Des 19(11): 2101-2113, 2013.

28 Mishra A and Palanivelu K: The effect of curcumin (turmeric) on Alzheimer's disease: an overview. Ann Indian Acad Neurol 11(1): 13-19, 2008.

29 Anggakusma, Colpitts C C, Schang L M, Rachmawati H, Frentzen A, Pfaender A, Behrendt A, Behrendt P, Brown R J, Bankwitz D, Steinmann J, Ott M, Meuleman P, Rice C M, Ploss A, Pieschmann T and Steinmann E: Turmeric curcumin inhibits entry of all hepatitis C virus genotypes into human liver cells. Gut 63(7): 1137:1149, 2014.

30 Chandran B and Goel A: A randomized, pilot study to assess the efficacy and safety of curcumin in patients with active rheumatoid arthritis. Phytother Res 26(11): 1719: 1725, 2012.

31 Wahlstrom B and Blennow G: A study on the fate of curcumin in the rat. Acta Pharmacol Toxicol (Copenh) 43: 86-92, 1978.

32 Storka A, Vcelar B, Klickovic U, Gouya G, Weisshaar S, Aschauer S, Bolger G, Helson L and Wolzt M: Safety, tolerability and pharmacokinetics of liposomal curcumin in healthy humans. Int J Clin Pharmacol Ther 53(1): 54-65, 2015.

33 Sharma R A, Euden S A, Platton S L, Cooke D N, Shafayat A, Hewitt H R, Marczylo T H, Morgan B, Hemingway D, Plummer S M, et al. Phase I clinical trial of oral curcumin: biomarkers of systemic activity and compliance. Clin Cancer Res 10: 6847-6854, 2004.

34 Aggarwal B B, Kumar A and Bharti A C: Anticancer potential of curcumin: preclinical and clinical studies. Anticancer Res 23(1A): 363-398, 2003.

35 Cheng A L, Hsu C H, Lin J K, Hsu M M, Ho Y F, Shen T S, Ko J Y, Lin J T, Lin B R, Ming-Shiang W, Yu H S, Jee S H, Chen G S, Chen T M, Chen C A, Lai M K, Pu Y S, Pan M R, Wang Y J, Tsai C C and Hsieh C Y: Phase I clinical trial of curcumin, a chemopreventive agent, in patients with high-risk or pre-malignant lesions. Anticancer Res 21(4B): 2895-900, 2001.

36 Sordillo P P and Helson L: Suppression of cytokine release and cytokine storm: a potential therapy for patients with Ebola and other viral infections. In Vivo 29: 1-4, 2015.

37 Chan M M: Inhibition of tumor necrosis factor by curcumin, a phytochemical. Biochem Pharmacol 49: 1551-1556, 1995.

38 Leow P C, Tian Q, Ong Z Y, Yang Z and Ee P L: Antitumor activity of natural compounds, curcumin and PKF118-310, as Wnt/β-catenin antagonists against human osteosarcoma cells. Invest New Drugs 28: 766-782, 2010.

39 Subramaniam D, Ponnurangam S, Ramamoorthy P, Standling D, Battafarano R J, Anant S and Sharma P: Curcumin induces cell death in esophageal cancer cells through modulating notch signaling. PloS One 7: e30590, 2012.

40 Elamin M H, Shinwari Z, Hendrayani S F, Al-Hindi H, Al-Shail E, Khafaga Y, Al-Kofide A and Aboussekhra A: Curcumin inhibits the Sonic Hedgehog signaling pathway and triggers apoptosis in medulloblastoma cells. Mol Carcinog 49: 302-314, 2010.

41 Alexandrow M G, Song L J, Altiok S, Haura E B and Kumar N B: Curcumin: a novel Stat3 pathway inhibitor for chemoprevention of lung cancer. Eur J Cancer Prev 21(5): 407-412, 2012.

42 Chiu S S, Liu E, Majeed M, Vishwanatha J K, Ranjan A P, Maitra A, Pramanik D, Smith J A and Helson L:

43 Priyadarsini K I: The chemistry of curcumin: from extraction to therapeutic agent. Molecules 19: 20091-20112, 2014.

44 Gao X, Deeb D, Jiang H, Liu Y B, Dulchavsky A S and Gautam S C: Curcumin differentially sensitizes malignant glioma cells to TRAIL/Apo2L-mediated apoptosis through activation of procaspases and release of cytochrome c from mitochondria. J Exp Ther Oncol 5: 39-48, 2005.

45 Kim S Y, Jung S H and Kim H S. Curcumin is a potent broad spectrum inhibitor of matrix metalloproteinase gene expression in human astroglioma cells. Biochem Biophys Res Commun 337: 510-516, 2005.

46 Nagai S, Kurimoto M, Washiyama K, Hirashima Y, Kumanishi Y and Endo S: Inhibition of cellular proliferation and induction of apoptosis by curcumin in human malignant astrocytoma cell lines. J Neurooncol 74: 105-111, 2005.

47 Woo M S, Jung S H, Kim S Y, Hyun J W, Ko K H, Kim W K, et al: Curcumin suppresses phorbol ester-induced matrix metalloproteinase-9 expression by inhibiting the PKC to MAPK signaling pathways in human astroglioma cells. Biochem Biophys Res Commun 335: 1017-1025, 2005.

48 Belkaid A, Copland I B, Massillon D and Annabi B: Silencing of the human microsomal glucose-6-phosphate translocase induces glioma cell death: potential new anticancer target for curcumin. FEBS Lett 580: 3746-3752, 2006.

49 Karmakar S, Banik N L, Patel S J and Ray S K: Curcumin activated both receptor mediated and mitochondria-mediated proteolytic pathways for apoptosis in human glioblastoma T98G cells. Neurosci Lett 407:53-8, 2006.

50 Aoki H, Takada Y, Kondo S, Sawaya R, Aggarwal B B and Kondo Y: Evidence that curcumin suppresses the growth of malignant gliomas in vitro and in vivo through induction of autophagy: role of Akt and extracellular signal-regulated kinase signaling pathways. Mol Pharmacol 72: 29-39, 2007.

51 Choi B H, Kim C G, Bae Y, Lim Y, Lee Y H, and Shin S Y: p21Waf1/Cip1 expression by curcumin in U-87MG human glioma cells: role of early growth response-1 expression. Cancer Res 68: 1369-1377, 2008.

52 Senft C, Polacin M, Priester M, Seifer V, Kögel D and Weissenberger J: The nontoxic natural compound Curcumin exerts anti-proliferative, anti-migratory, and anti-invasive properties against malignant gliomas. Cancer 10: 491, 2010.

53 Dhandapani K M, Mahesh V B and Brann D W. Curcumin suppresses growth and chemoresistance of human glioblastoma cells via AP-1 and NFkappaB transcription factors. J Neurochem 102: 522-38, 2007.

54 Zanotto-Filho A, Braganhol E, Edelweiss M I, Behr G A, Zanin R, Schröder R, Simões-Pires A, Battastini A M and Moreira J C: The curry spice curcumin selectively inhibits cancer cells growth in vitro and in preclinical model of glioblastoma. J Nutr Biochem. 23(6): 591-601, 2012.

55 Perry M C, Demeule M, Régina A, Moumdjian R and Béliveau R: Curcumin inhibits tumor growth and angiogenesis in glioblastoma xenografts. Mol Nutr Food Res. 54(8): 1192201, 2010.

56 Beier D, Schulz J B and Beier C P: Chemoresistance of glioblastoma cancer stem cells—much more complex than expected. Mol Cancer 10: 128, 2011.

57 Bleau A M, Hambardzumyan D, Ozawa, T, Fomchenko E I, Huse J T, Brennan C W and Holland E C: PTEN/PI3K/Akt pathway regulates the side population phenotype and ABCG2 activity in glioma tumor stem-like cells. Cell Stem Cell 4: 226-235, 2009.

58 Schiffer D, Mellai M, Annovazzi L, Piazzi A, Monzeglio O and Caldera V: Glioblastoma cancer stem cells: basis for a functional hypothesis. Stem Cell Discovery 2 (3) 122-131, 2012.

59 Fong D, Yeh A, Naftalovich R, Choi T H and Chan M M: Curcumin inhibits the side population (SP) phenotype of the rat C6 glioma cell line: towards targeting of cancer stem cells with phytochemicals. Cancer Lett 293(1): 65-72, 2010.

60 Zhuang W, Long L, Zheng B, Ji W, Yang N, Zhang Q and Liang Z: Curcumin promotes differentiation of glioma-initiating cells by inducing autophagy. Cancer Science 103(4): 684-690, 2012.

61 Ganta S and Amiji M: Coadministration of paclitaxel and curcumin in nanoemulsion formulations to overcome multidrug resistance in tumor cells. Mol Pharm 6: 928-39, 2009.

62 Bisht S, Mizuma M, Feldmann G, Ottenhof N A, Hong S M, Pramanik D, et al: Systemic administration of polymeric nanoparticle-encapsulated curcumin (Nano-Curc) blocks tumor growth and metastases in preclinical models of pancreatic cancer. Mol Cancer Ther 9: 2255-2264, 2010.

63 Helson L: Curcumin (diferoylmethane) delivery methods: a review. Biofactors 39: 21-26, 2013.

64 Séhédic D, Cikankowitz A, Hindré F, Davodeau F and Garcion E: Nanomedicine to overcome radioresistance in glioblastoma stem-like cells and surviving clones. Trends Pharmacol Sci 36(4): 236-25, 2015.

65 Zanotto-Filho A, Coradini K, Braganhol E, Schröder R, de Oliveira C M, SimõesPires A et al: Curcumin-loaded lipid-core nanocapsules as a strategy to improve pharmacological efficacy of curcumin in glioblastoma treatment. Eur J Pharm Biopharm 83(2): 156-67, 2013.

66 Lim K J, Maitra A, Bisht S, Eberhart C and Bar E: Using nanocurcumin to treat medulloblastoma and glioblastoma. Cancer Res 70: 4440, 2010.

67 Langone P, Debata P R, Inigo Jdel R, Dolai S, Mukherjee S, Halat P, Mastroianni K, Curcio G M, Castellanos M R, Raja K and Banerjee P: Coupling to a glioblastoma directed antibody potentiates antitumor activity of curcumin. Int J Cancer 135(3): 7109, 2014.

68 Ramachandran C, Nair S M, Escalon E and Melnick S J: Potentiation of etoposide and temozolomide cytotoxicity by curcumin and turmeric force in brain tumor cell lines. J Complement Integr Med 9: Article 20, 2012.

69 Yin H, Zhou Y, Wen C, Zhou C, Zhang W, Hu X, Wang L, You C, Shao J: Curcumin sensitizes glioblastoma to temozolomide by simultaneously generating ROS and disrupting AKT/mTOR signaling. Oncology Reports 32(4): 1610-1616, 2014.

70 Zanotto-Filho A, Braganhol E, Edelweiss M I, Behr G A, Zanin R, Schröder R, Simões-Pires A, Battastini A M and Moreira J C: The curry spice curcumin selectively inhibits cancer cells growth in vitro and in preclinical model of glioblastoma. J Nutr Biochem 23(6): 591-601, 2012.

71 Wu H, Liu Q, Cai T, Chen Y D and Wang Z F: Induction of microRNA-146a is involved in curcumin-mediated enhancement of temozolomide cytotoxicity against human glioblastoma. Mol Med Rep. doi:10.3892/mmr2015.4087.

72 Hossain M M, Banik N K and Ray S K: Synergistic anti-cancer mechanisms of curcumin and paclitaxel for growth inhibition of human brain tumor stem cells and LN18 and U138MG cells. Neurochem Int 61: 1102-111, 2012.

73 Lim K J, Bisht S, Bar E E, Maitra A and Eberhart C G: A polymeric nanoparticle formulation of curcumin inhibits growth, clonogenicity and stem-like fraction in malignant brain tumors. Cancer Biol Ther 11: 464-473, 2011.

74 Sordillo P P and Helson L: Curcumin and cancer stem cells: curcumin has asymmetrical effects on cancer and normal stem cells. Anticancer Research 35: 599-614, 2015.

75 Almanaa T N, Geusz M E and Jamasbi R J: Effects of curcumin on stem-like cells in human esophageal squamous carcinoma cell lines. BMC Complementary and Alternative Medicine 12: 195, 2012.

76 Batth B K, Tripathi R and Srinivas U K: Curcumin-induced differentiation of mouse embryonal carcinoma PCC4 cells. Differentiation 68: 133-140, 2001.

77 Li X, Lewis M T, Huang J, Gutierrez C, Osborne C K, Wu M F, Hilsenbeck S G, Pavlick A, Zhang X, Chamness G C, Wong H, Rosen J and Chang J C: Intrinsic resistance of tumorigenic breast cancer cells to chemotherapy. J Natl Cancer Inst 100: 672-679, 2008.

78 Moussavi M, Assi K, Gómez-Muñoz A and Salh B: Curcumin mediates ceramide generation via the de novo pathway in colon cancer cells. Carcinogenesis 27(8): 1636-44, 2006.

79 Grammatikos G, Teichgraber V, Carpinteiro A, Trarbach T, Weller M, et al: Overexpression of acid sphingomyelinase sensitizes glioma cells to chemotherapy. Antioxid Redox Signal 9: 1449-1456, 2007.

80 Hara S, Nakashima S, Kiyono T, Sawada M, Yoshimura S, et al: p53-Independent ceramide formation in human glioma cells during gamma-radiation-induced apoptosis. Cell Death Differ 11: 853-861, 2004.

81 Riboni L, Campanella R, Bassi R, Villani S N, et al. Ceramide levels are inversely associated with malignant progression of human glial tumors. Glia 39: 105-113, 2002.

82 Giussani P, Bassi R, Anelli V, Brioschi L, De Zen F, et al. Glucosylceramide synthase protects glioblastoma cells against autophagic and apoptotic death induced by temozolomide and Paclitaxel. Cancer Invest 30: 27-37, 2012.

83 Manago A, Becker K A, Carpinteiro A, Wilker B, Soddemann M, Seitz A P, Edwards M J, Grassme H, Szabo I and Gulbins E: *Pseudomonas aeruginosa* pyocyanin induces neutrophil death via mitochondrial reactive oxygen species and mitochondrial acid sphingomyelinase. Antioxid Redox Signal 22: 1097-1110, 2015.

84 Hatanaka Y, Fujii J, Fukutomi T, Watanabe T, Che W, Sanada Y, Igarashi Y and Taniguchi N: Reactive oxygen species enhances the induction of inducible nitric oxide synthase by sphingomyelinase in RAW264.7 cells. Biochem Biophs Acta 1393: 203-210, 1998.

85 Castillo S S, Levy M, Thaikoottathil J V and Goldkorn T: Reactive nitrogen and oxygen species activate different sphingomyelinases to induce apoptosis in airway epithelial cells. Exp Cell Res 313: 2680-2686, 2007.

What is claimed is:

1. A method for treating a glioblastoma in a human subject comprising the steps of:
   identifying the human subject in need of treatment of a glioblastoma, wherein the human subject is no longer responsive to at least one of chemotherapy, surgery, or radiation therapy; and
   administering to the human subject a therapeutically effective amount of a composition consisting of:
   an amount of a curcumin or curcuminoids and one or more empty liposomes and administered prior to, concomitantly, or after administration of the curcumin or curcuminoids, that is effective for treating the glioblastoma, wherein the empty liposomes eliminate the QT prolongation caused by the curcumin or curcuminoids; and
   at least one chemotherapeutic agent, wherein the amount of the curcumin or curcumioids and the chemotherapeutic agent is synergistic to treat the glioblastoma that is no longer responsive to at least one of chemotherapy, surgery, or radiation therapy, wherein the glioblastoma cells are sensitized to an agent to which they have become refractory as a result of the increased ceramide production in the glioblastoma cell.

2. The method of claim 1, wherein the chemotherapeutic agent is selected from at least one of etoposide, doxorubicin, cisplatin, paclitaxel, carmustine, lomustine, ceramide and phosphorylcholine.

3. The method of claim 1, wherein the QT prolongation is LQTS.

4. The method of claim 3, wherein the curcumin or curcuminoids, or empty liposomes are administered intravenously.

5. The method of claim 1, wherein the composition increases ceramide production of the glioblastoma cell.

6. The method of claim 1, wherein the composition increases phosphorylcholine production of the glioblastoma cell.

7. The method of claim 1, wherein the glioblastoma cells are sensitized to an agent to which they have become refractory as a result of increased phosphorylcholine production in the glioblastoma cell.

* * * * *